(12) United States Patent
Wake

(10) Patent No.: US 10,219,678 B2
(45) Date of Patent: Mar. 5, 2019

(54) INSERTION PORTION MOUNTED TOOL OF INSERTION INSTRUMENT AND INSERTION SYSTEM

(71) Applicant: OLYMPUS CORPORATION, Tokyo (JP)

(72) Inventor: Fuminori Wake, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/486,465

(22) Filed: Apr. 13, 2017

(65) Prior Publication Data
US 2017/0215701 A1 Aug. 3, 2017

Related U.S. Application Data

(63) Continuation of application No. PCT/JP2016/054694, filed on Feb. 18, 2016.

(30) Foreign Application Priority Data

Mar. 19, 2015 (JP) .................. 2015-056354

(51) Int. Cl.
*A61B 1/00* (2006.01)
*A61M 25/10* (2013.01)

(52) U.S. Cl.
CPC ........ *A61B 1/00082* (2013.01); *A61B 1/0014* (2013.01); *A61B 1/00101* (2013.01);
(Continued)

(58) Field of Classification Search
CPC ............ A61B 1/00082; A61B 1/00156; A61B 1/00149; A61B 1/00151; A61B 1/00154;
(Continued)

(56) References Cited

U.S. PATENT DOCUMENTS

2007/0112250 A1* 5/2007 Kura .................. A61B 1/00135
600/114
2007/0276181 A1 11/2007 Terliuc
(Continued)

FOREIGN PATENT DOCUMENTS

CN 103142199 A 6/2013
JP 2009-195321 A 9/2009
(Continued)

OTHER PUBLICATIONS

International Search Report dated May 17, 2016 issued in PCT/JP2016/054694.

*Primary Examiner* — Timothy J Neal
(74) *Attorney, Agent, or Firm* — Scully, Scott, Murphy & Presser, P.C.

(57) ABSTRACT

An insertion portion mounted tool of an insertion instrument includes: an expansion and retraction section provided on an outer circumferential side of an insertion portion so as to be movable forward and backward in a longitudinal direction, and configured to be expanded in the subject by an operation from outside of the subject to thereby be held by an inner wall of the subject; a positioning portion that defines a range in which the expansion and retraction section is movable forward and backward in the longitudinal direction with respect to the insertion portion; and a rotational movement restriction portion that restricts an angle in which the expansion and retraction section is rotationally moved in an outer circumferential direction on an outer circumference of the insertion portion.

11 Claims, 11 Drawing Sheets

(52) U.S. Cl.
CPC ...... *A61B 1/00135* (2013.01); *A61B 1/00154* (2013.01); *A61M 25/1018* (2013.01); *A61M 2025/1084* (2013.01)

(58) Field of Classification Search
CPC .............. A61B 1/0016; A61B 1/00131; A61B 1/00133; A61B 1/00071; A61B 1/00073; A61B 1/00075; A61M 25/1018; A61M 2025/1084
See application file for complete search history.

(56) References Cited

U.S. PATENT DOCUMENTS

| | | |
|---|---|---|
| 2008/0064930 A1 | 3/2008 | Terliuc |
| 2008/0091062 A1* | 4/2008 | Turliuc .............. A61B 1/00082 600/104 |
| 2008/0091063 A1 | 4/2008 | Terliuc |
| 2008/0091068 A1 | 4/2008 | Terliuc |
| 2010/0240955 A1* | 9/2010 | Sinai .................. A61B 1/00082 600/116 |
| 2015/0335229 A1 | 11/2015 | Terliuc |

FOREIGN PATENT DOCUMENTS

| | | |
|---|---|---|
| JP | 2011-024829 A | 2/2011 |
| JP | 2012-200552 A | 10/2012 |
| JP | 2013-085812 A | 5/2013 |

* cited by examiner

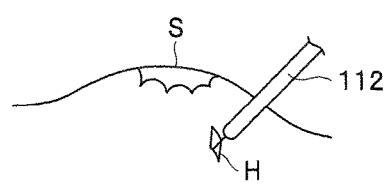
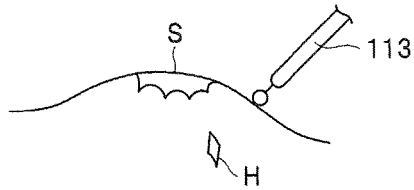
FIG. 8A  FIG. 8B
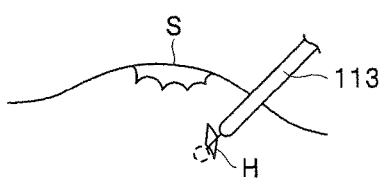
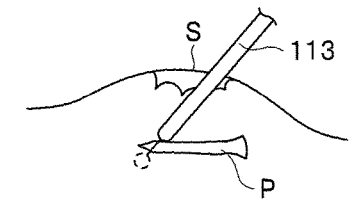
FIG. 8C  FIG. 8D
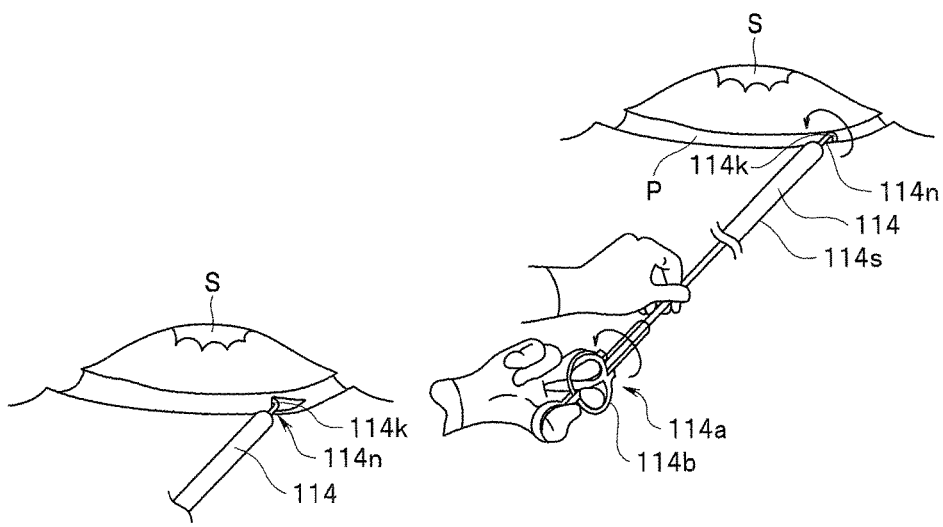
FIG. 9A  FIG. 9B

INSERTION PORTION MOUNTED TOOL OF INSERTION INSTRUMENT AND INSERTION SYSTEM

CROSS REFERENCE TO RELATED APPLICATION

This application is a continuation application of PCT/JP2016/054694 filed on Feb. 18, 2016 and claims benefit of Japanese Application No. 2015-056354 filed in Japan on Mar. 19, 2015, the entire contents of which are incorporated herein by this reference.

BACKGROUND OF THE INVENTION

1. Field of the Invention

The present invention relates to an insertion portion mounted tool of an insertion instrument and an insertion system that include an expansion and retraction section which is provided to an outer circumference of an insertion portion of an insertion instrument to be inserted into a subject and which is configured expanded to be held by an inner wall of the subject.

2. Description of the Related Art

In recent years, insertion instruments to be inserted into a subject or an object, for example, endoscopes have been widely used in medical fields and industrial fields.

Endoscopes for use in medical fields are capable of observing an organ in a body cavity using an optical system provided in an insertion portion by the elongated insertion portion being inserted into the body cavity as a subject, and performing various kinds of treatment, as needed, through the use of a treatment instrument inserted into a treatment instrument channel provided in the endoscope.

In addition, endoscopes for use in industrial fields are capable of performing observation and inspection of a flaw, corrosion, and the like of a site to be inspected in an object using an optical system provided in an insertion portion by the elongated insertion portion being inserted into the object such as a jet engine, a piping of a factory, or the like.

A procedure is well-known in which an insertion portion is inserted into a subject and a site to be examined is treated by using a treatment instrument inserted into a channel in the insertion portion by moving the insertion portion in a longitudinal direction of the insertion portion (hereinafter, shortly referred to as longitudinal direction) while observing the site to be examined with an optical system.

For example, in endoscopes for use in medical fields, a procedure is well-known in which, in a state where an insertion portion is inserted into a body cavity and a tissue to be treated in the body cavity is observed with an optical system, a treatment instrument inserted in a channel is protruded forward in the longitudinal direction of the insertion portion (hereinafter shortly referred to as forward) from the distal end in the longitudinal direction of the insertion portion (hereinafter, shortly referred to as distal end), and thereafter the tissue to be treated is dissected and resected by using the treatment instrument by moving the insertion portion in the longitudinal direction.

As one example, endoscopic submucosal dissection (hereinafter, referred to as ESD) is well-known, in which, in the state where an insertion portion is inserted into a body cavity and a carcinoma tissue in the body cavity is observed with an optical system, a high-frequency electrocautery scalpel inserted into a channel is protruded forward from the distal end of the insertion portion, and thereafter the carcinoma tissue raised in advance by injecting specialized-purpose liquid is removed with the high-frequency electrocautery scalpel, by moving the insertion portion forward and backward in the longitudinal direction of the insertion portion (hereinafter, just referred to as forward and backward).

In addition, as another example, endoscopic mucosal resection (hereinafter, referred to as EMR) is well-known, in which, in the state where an insertion portion is inserted into a body cavity and a carcinoma tissue in the body cavity is observed with an optical system, a snare inserted into a channel is protruded forward from the distal end of the insertion portion to be hooked on the carcinoma tissue raised in advance by injecting specialized-purpose liquid, and thereafter the carcinoma tissue is removed by constricting the snare while applying high-frequency current to the snare.

Japanese Patent Application Laid-Open Publication No. 2013-85812 discloses a configuration of an endoscope system including an overtube as an insertion portion mounted tool in which an insertion portion is inserted so as to be movable forward and backward, the overtube including, on the outer circumference on the distal end side in the longitudinal direction thereof (hereinafter, just referred to as distal end side), a balloon as an expansion and retraction section which is expandable and contractible in a subject by an operation from outside of the subject and expanded to be held by the inner wall of the subject. With the endoscope system, the balloon is expanded to be held by the body wall in the subject after the overtube having been inserted into the subject together with the insertion portion, and thereby the position of the distal end side of the overtube is fixed, to prevent the position in the longitudinal direction and the outer circumferential direction of the distal end side of the insertion portion in the overtube from being largely displaced in the subject.

In addition, Japanese Patent Application Laid-Open Publication No. 2011-24829 discloses a configuration of an endoscope system in which a balloon as an insertion portion mounted tool is directly fixed to the outer circumference of the distal end side of the insertion portion, to prevent the position in the longitudinal direction and the outer circumferential direction of the distal end side of the insertion portion from being greatly displaced in the subject, through the use of the balloon.

SUMMARY OF THE INVENTION

An insertion portion mounted tool of an insertion instrument according to one aspect of the present invention is an insertion portion mounted tool of an insertion instrument which is mounted to an insertion portion of the insertion instrument to be inserted into a subject, and includes: an expansion and retraction section provided on an outer circumferential side of the insertion portion so as to be movable forward and backward in a longitudinal direction of the insertion portion, and configured to be expanded in the subject by an operation from outside of the subject to thereby be held by an inner wall of the subject; a positioning portion that defines a range in which the expansion and retraction section is movable forward and backward in the longitudinal direction with respect to the insertion portion; and a rotational movement restriction portion that restricts an angle in which the expansion and retraction section is rotationally moved in an outer circumferential direction of the insertion portion on an outer circumference of the insertion portion.

In addition, an insertion system according to one aspect of the present invention includes: the insertion portion mounted tool of the insertion instrument; and the insertion instrument including the insertion portion to which the insertion portion mounted tool of the insertion instrument is mounted.

BRIEF DESCRIPTION OF THE DRAWINGS

FIG. 8A is a perspective view illustrating a procedure for forming a hole on a mucosa around a lesional mucosa part with an incision tool.

FIG. 8B is a perspective view illustrating a state where a high-frequency knife is protruded in a subject through a channel of the endoscope.

FIG. 8C is a perspective view illustrating a state where a distal end of the high-frequency knife in FIG. 8B is inserted in the hole formed by the incision tool.

FIG. 8D is a perspective view illustrating an incision operation of the lesional mucosa part with the high-frequency knife.

FIG. 9A is a perspective view illustrating a state where a distal end of a dissection tool is hooked on a slit formed by the incision with the high-frequency knife.

FIG. 9B is a perspective view illustrating an operation of adjusting a direction of a flexing portion of the dissection tool in FIG. 9A.

DETAILED DESCRIPTION OF THE PREFERRED EMBODIMENTS

Hereinafter, embodiments of the present invention will be described with reference to drawings. Note that each of the drawings is a pattern diagram, and care should be taken to the fact that the relationship between the thicknesses and widths of the respective members, a ratio of the thickness of a certain member to that of another member, and the like are different from the actual ones. It is needless to say that each of the drawings includes a different relationship and ratio among the dimensions of the members.

Hereinafter, an insertion instrument will be described by taking an endoscope as an example. Therefore, an insertion portion mounted tool of an insertion instrument will be described by taking the insertion portion mounted tool of the endoscope as an example, and an insertion system will be described by taking an endoscope system including the endoscope and the insertion portion mounted tool of the endoscope as an example.

First Embodiment

Figure 1:
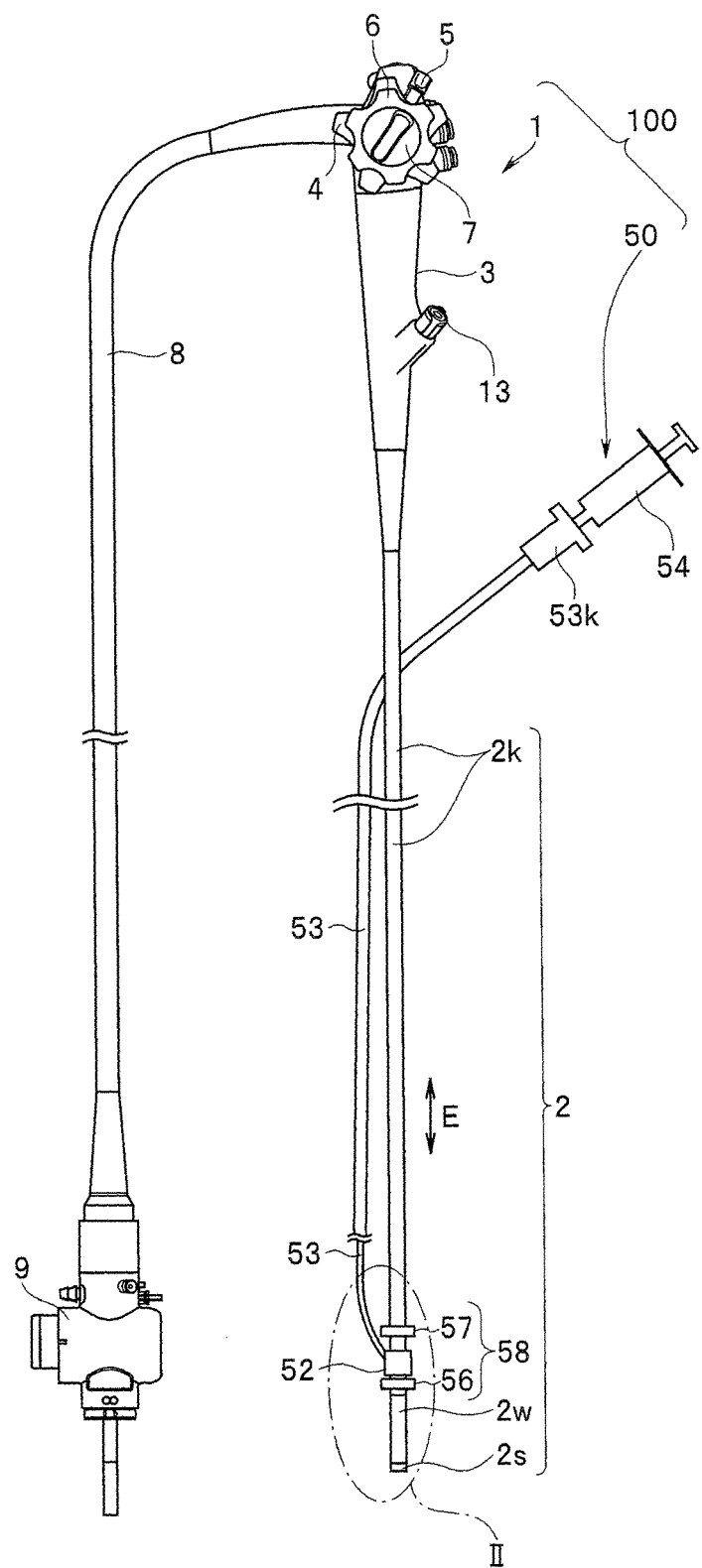
FIG. 1 is a view schematically illustrating an endoscope system including an insertion portion mounted tool of an endoscope according to a first embodiment.

FIG. 1 is a view schematically illustrating an endoscope system including an insertion portion mounted tool of an endoscope according to the present embodiment.

As shown in FIG. 1, an endoscope system 100 includes a main part configured by an endoscope 1, and an insertion portion mounted tool 50.

The endoscope 1 includes a main part configured by an insertion portion 2 to be inserted into a subject, an operation portion 3 provided continuously with a proximal end side in a longitudinal direction E (hereinafter, just referred to as proximal end side) of the insertion portion 2, a universal cord 8 extended from the operation portion 3, and a connector 9 provided at an extension end of the universal cord 8. Note that the endoscope 1 is electrically connected with an external apparatus such as a control apparatus, an illumination apparatus, or the like, through the connector 9.

The operation portion 3 is provided with an up/down bending operation knob 4 for bending a bending portion 2w, to be described later, of the insertion portion 2 in up and down directions, and a right/left bending operation knob 6 for bending the bending portion 2w in right and left directions.

In addition, the operation portion 3 is provided with a fixing lever 5 that fixes a rotational movement position of the up/down bending operation knob 4 and a fixing knob 7 that fixes a rotational movement position of the right/left bending operation knob 6.

Furthermore, the operation portion 3 includes a treatment instrument insertion port 13 through which a treatment instrument or the like is inserted into a channel 2n to be described later.

The insertion portion 2 is formed in an elongated shape and includes a distal end portion 2s, the bending portion 2w, and a flexible tube portion 2k in this order from the distal end side along the longitudinal direction E.

The bending portion 2w is bent in four directions, i.e., up, down, right, and left directions, for example, by rotational movement operation of the up/down bending operation knob 4 and the right/left bending operation knob 6, to allow an observation direction of an optical system of an image pickup unit, not shown, provided in the distal end portion 2s to be varied, and improve insertion performance of the distal end portion 2s into the subject. Furthermore, the flexible tube portion 2k is provided continuously with the proximal end side of the bending portion 2w.

In addition, the channel 2n (see FIG. 2), a distal end of which is open on a distal end surface 2sm (see FIG. 2) of the distal end portion 2s and a part of which is diverged toward the treatment instrument insertion port 13 formed on the operation portion 3, is provided in the insertion portion 2, the operation portion 3, the universal cord 8, and the connector 9. The channel 2n constitutes a conduit through which the treatment instrument or the like is inserted, and serves also as a suction conduit through which a body fluid and the like in a body cavity are sucked.

The insertion portion mounted tool 50, a part of which is mounted to the insertion portion 2, includes a main part configured by an expansion and retraction section 52, rotational movement restriction portions 52at (see FIG. 2) which are second abutting portions, a fluid conduit 53, a fluid supplying/discharging member 54 which is attachable to and detachable from a pipe sleeve 53k at the proximal end of the fluid conduit 53, a rotational movement restriction portion 55 (see FIG. 2) which is a first abutting portion, and a positioning portion 58.

Note that the rotational movement restriction portions are not limited to the first and second abutting portions, and may be configured by combining another first abutting portion and another second abutting portion such as a protrusion portion and a wall, a protrusion portion and a groove, or the like, which are abutted against each other to restrict the rotation angle.

Figure 2:
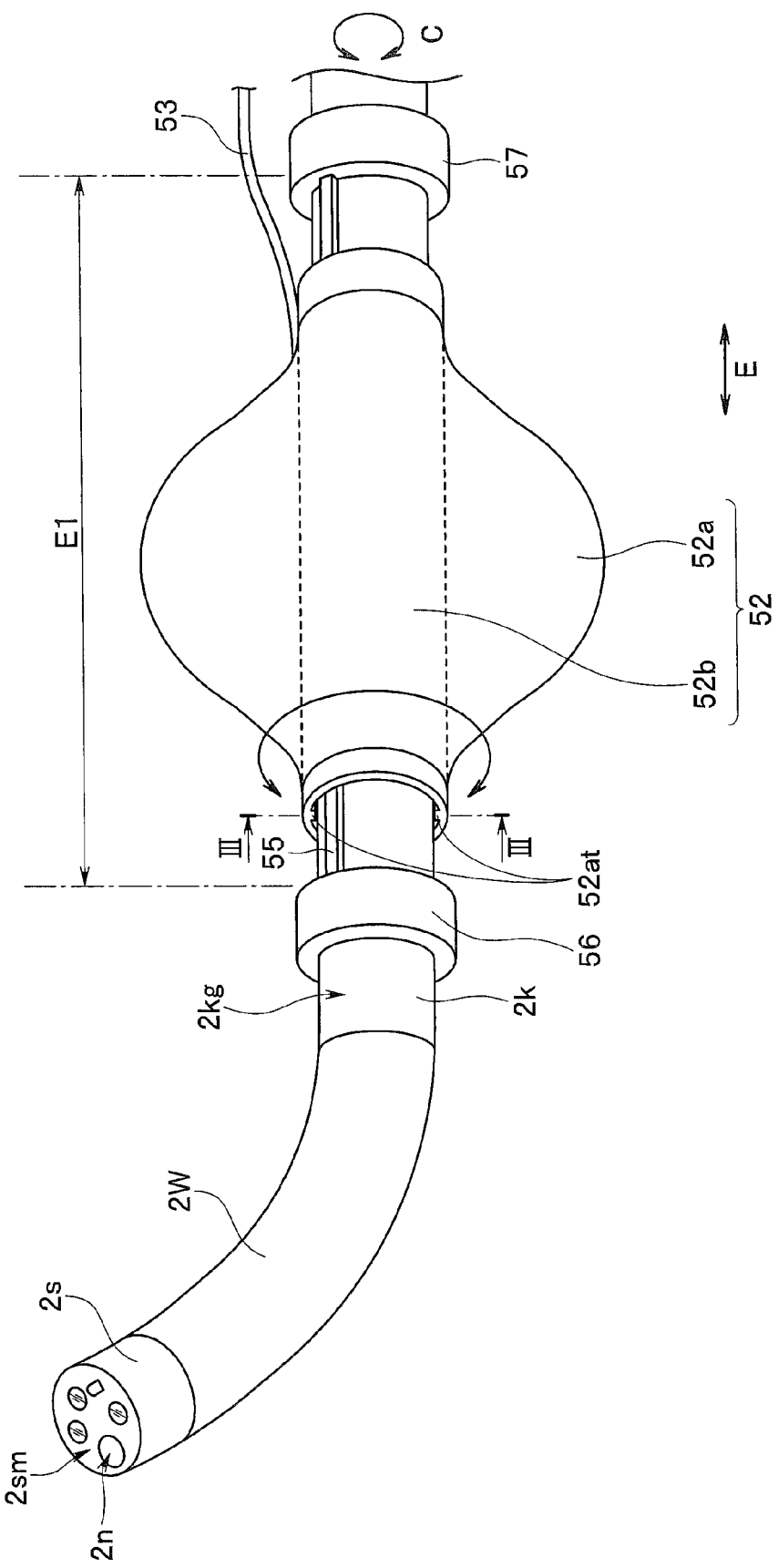
FIG. 2 is a partial perspective view illustrating, in an enlarged manner, a part surrounded by line II in an insertion system in FIG. 1 in a state where a bending portion is bent and an expansion and retraction section is expanded.
Figure 3:
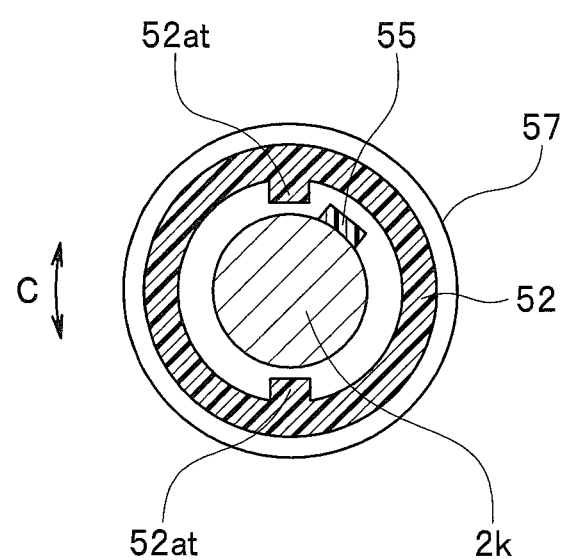
FIG. 3 is a cross-sectional view of the endoscope system along line III-III in FIG. 2 in a state where the expansion and retraction section in FIG. 2 is contracted.

Next, the configuration of the insertion portion mounted tool 50 will be described with reference to FIGS. 2 to 7. FIG. 2 is a partial perspective view illustrating, in an enlarged manner, the part surrounded by the line II in the insertion system in FIG. 1 in the state where the bending portion is bent and the expansion and retraction section is expanded, and FIG. 3 is a cross-sectional view of the endoscope system along the line III-III in FIG. 2 in the state where the expansion and retraction section in FIG. 2 is contracted.

Figure 4:
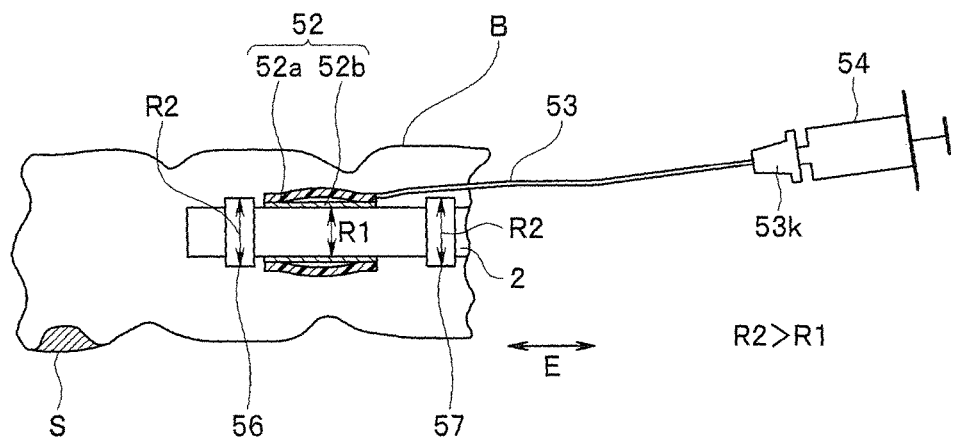
FIG. 4 is a view schematically illustrating a state where a distal end side of the endoscope system in FIG. 2 is inserted into a subject and the expansion and retraction section in FIG. 2 is contracted, with only the expansion and retraction section shown in a cross section.
Figure 5:
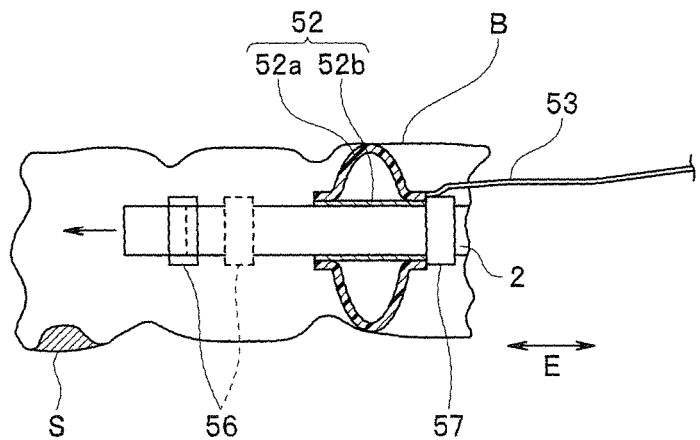
FIG. 5 is a view schematically illustrating a state where the expansion and retraction section in FIG. 4 is expanded and held by an inner wall of the subject, the insertion portion is moved forward, and the expansion and retraction section is abutted against a ring-shaped member located at a rear side in a positioning portion.

In addition, FIG. 4 is a view schematically illustrating the state where the distal end side of the endoscope system in FIG. 2 is inserted into the subject and the expansion and retraction section in FIG. 2 is contracted, with only the expansion and retraction section shown in a cross section, and FIG. 5 is a view schematically illustrating the state where the expansion and retraction section in FIG. 4 is expanded and held by the inner wall of the subject, the insertion portion is moved forward, and the expansion and retraction section is abutted against the ring-shaped member located at the rear side in the positioning portion.

Figure 6:
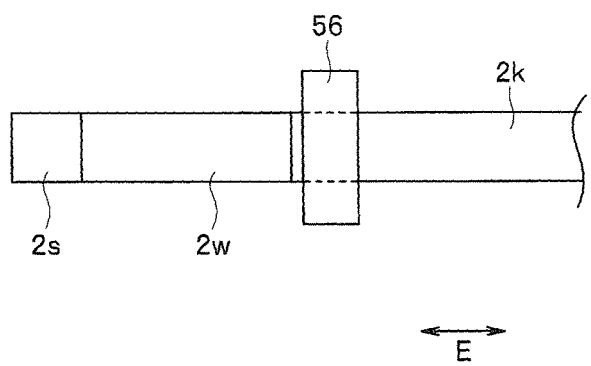
FIG. 6 is a view schematically illustrating a configuration in which a ring-shaped member located at a front side in the positioning portion in FIG. 2 is provided immediately behind the bending portion.
Figure 7:
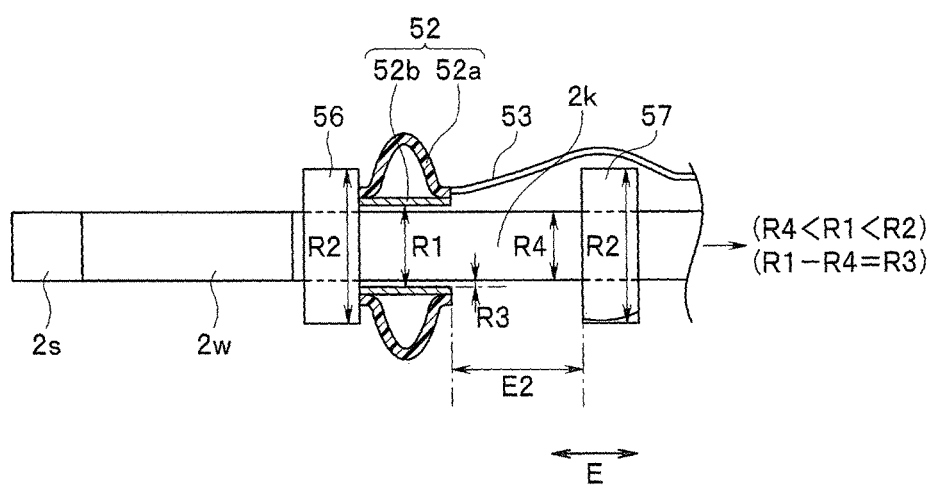
FIG. 7 is a view schematically illustrating a state where the insertion portion in FIG. 5 is moved backward, and the expansion and retraction section is abutted against the ring-shaped member located at the front side.

Furthermore, FIG. 6 is a view schematically illustrating the configuration in which the ring-shaped member located at the front side in the positioning portion in FIG. 2 is provided immediately behind the bending portion, and FIG. 7 is a view schematically illustrating the state where the insertion portion in FIG. 5 is moved backward, and the expansion and retraction section is abutted against the ring-shaped member located at the front side.

As shown in FIGS. 1 to 5, and FIG. 7, the positioning portion 58 is fixed to the outer circumference of the insertion portion 2, and includes, for example, two ring-shaped members 56, 57 fixed so as to be separated from each other so as to have a predetermined space E1 therebetween in the longitudinal direction E.

Note that the ring-shaped members 56, 57 are made of a flexible material such as resin, silicone, or the like, or made of metal with sufficiently small width so as not to impair the flexibility of the insertion portion 2.

In addition, the ring-shaped members 56, 57 are fastened to the outer circumference of the insertion portion with bands, not shown, or by bore diameters of the ring-shaped members 56, 57 being formed to be smaller than the outer diameter of the insertion portion, to be fixed to the insertion portion 2 directly, not through other members. Therefore, the ring-shaped members 56, 57 may be configured to be attachable to or detachable from the outer circumference of the insertion portion 2.

The expansion and retraction section 52 includes a main part configured by a tubular attaching portion 52b loosely fitted to the outer circumference of the insertion portion 2, and an expanding and contracting portion 52a provided to the attaching portion 52b.

The expansion and retraction section 52 includes the attaching portion 52b loosely fitted to the outer circumference of the insertion portion 2, to thereby be provided to the outer circumference of the insertion portion 2 directly, not through another member, so as to be movable forward and backward and rotationally movable in the outer circumferential direction C within a range E1 coincident with the predetermined space in the longitudinal direction E, which is restricted by the ring-shaped members 56 and 57.

Note that the ring-shaped members 56 and 57 are fixed at positions on the outer circumference of the insertion portion 2 so as to restrict the range within which the expansion and retraction section 52 is moved in the longitudinal direction E to a part other than the bending portion 2w.

Specifically, the ring-shaped members 56 and 57 are fixed to an outer circumference 2kg of the flexible tube portion 2k located more rearward in the longitudinal direction E (hereinafter, just referred to as rearward) than the bending portion 2w of the insertion portion 2. The reason is that the bending operation of the bending portion 2w is interfered, if the ring-shaped members 56 and 57 are fixed to the bending portion 2w.

The expansion and retraction section 52 includes the attaching portion 52b loosely fitted to the outer circumference 2kg of the flexible tube portion 2k, to thereby be configured to be movable forward and backward and rotationally movable in the outer circumferential direction C with respect to the outer circumference 2kg of the flexible tube portion 2k within the range E1 in the longitudinal direction E which is restricted by the ring-shaped members 56 and 57.

Note that the expansion and retraction section 52 may be configured to be movable only in the forward and backward directions with respect to the outer circumference 2kg of the flexible tube portion 2k, within the range E1 in the longitudinal direction E, and when the expansion and retraction section 52 is rotationally moved in the outer circumferential direction C, resistance may be applied to the rotational movement with a configuration in which friction is generated between the expansion and retraction section 52 and the outer circumference 2kg of the flexible tube portion 2k.

Note that, as shown in FIG. 6, it is preferable that the ring-shaped member 56 is fixed to a position immediately behind the proximal end of the bending portion 2w or a joint portion between the bending portion 2w and the flexible tube portion 2k.

Although the reason will be described later, in the state where the expanding and contracting portion 52a of the expansion and retraction section 52 is expanded to be held by the inner wall of the subject and the expansion and retraction section 52 is abutted against the ring-shaped member 56 as shown in FIG. 7, if the ring-shaped member 56 is fixed to the outer circumference 2kg of the flexible tube portion 2k at a position largely separated rearward from the proximal end of the bending portion 2w, the part of the insertion portion 2, which is more distal end side with respect to the expanding and contracting portion 52a held by the body wall, droops in the subject.

In addition, as shown in FIG. 7, the inner diameter R1 of the attaching portion 52b of the expansion and retraction section 52 is formed to be larger than the outer diameter R4 of the insertion portion 2 and smaller than the outer diameter R2 of the ring-shaped members 56 and 57 (R4<R1<R2).

According to such a configuration, the attaching portion 52b is surely abutted against the ring-shaped members 56 and 57, which allows the expansion and retraction section 52 to be movable forward and backward between the ring-shaped member 56 and the ring-shaped member 57 in the longitudinal direction E.

Therefore, as described later, in the state where the expanding and contracting portion 52a is expanded to be held by the inner wall of the subject, the distal end side of the insertion portion 2 is movable forward and backward within the range in which the attaching portion 52b abuts against the ring-shaped members 56 and 57.

Furthermore, a gap R3 between the outer circumference 2kg of the flexible tube portion 2k of the insertion portion 2 and the inner circumference of the attaching portion 52b (R3=R1−R4) is set to be in a range of values larger than 0 mm to equal to or smaller than 2.8 mm, for example.

The thickness of the thinnest part of the large intestine of a human being is known to be approximately 1.4 mm. Therefore, when the endoscope system 100 is inserted into the large intestine B (see FIG. 4), if the gap R3 is set to be larger than 2.8 mm, the intestinal wall folded into two is likely to be caught in the gap R3.

In other words, the gap R3 is set to be in a range of values larger than 0 mm and equal to or smaller than 2.8 mm, to thereby surely prevent the intestinal wall folded into two from being caught in the gap R3 when the endoscope system 100 is inserted into the large intestine B.

The expanding and contracting portion 52a of the expansion and retraction section 52 is, as shown in FIGS. 4 and 5, expandable and contractible in the subject by the operation from outside of the subject, and is made of a known balloon which is expanded to be held by the inner wall of the large intestine B as the subject, for example, as shown in FIG. 5.

Specifically, the distal end of the fluid conduit 53 configured by a tube or the like is connected with the expanding and contracting portion 52a, the fluid supplying/discharging member 54 configured by a syringe, for example, is connected with the pipe sleeve 53k provided at the proximal end of the fluid conduit 53, which is located outside the subject, and the expanding and contracting portion 52a is expandable and contractible by a gas being supplied to or discharged from the expanding and contracting portion 52a through the fluid conduit 53.

Note that the fluid supplying/discharging member 54 is not limited to a syringe, and may be made of any member as long as the member is capable of supplying and discharging a gas to and from the expanding and contracting portion 52a.

In addition, in the endoscope system 100 according to the present embodiment, the parts located outside the subject when the endoscope system 100 is inserted into the subject are only a part of the insertion portion 2, the operation portion 3, the universal cord 8, and the connector 9 in the endoscope 1, a part of the fluid conduit 53, and the fluid supplying/discharging member 54.

Specifically, when the endoscope system 100 is inserted into the large intestine B, for example, the parts contacting the anus are only the insertion portion 2 and a part of the fluid conduit 53.

In addition, as shown in FIG. 5, in the state where the expanding and contracting portion 52a is expanded in the large intestine B and held by the intestinal wall, for example, the distal end side of the insertion portion 2 is movable forward and backward in the range between the position at which the attaching portion 52b abuts against the ring-shaped member 57 and the position at which the attaching portion 52b abuts against the ring-shaped member 56, as shown in FIG. 7.

More specifically, through the use of the ring-shaped members 56 and 57, the expansion and retraction section 52 or the distal end side of the insertion portion 2 is set to be movable forward and backward within the range of 20 mm or more and 100 mm or less which is required for the ESD as described above.

That is, the predetermined space E1 in the longitudinal direction E between the ring-shaped member 56 and the ring-shaped member 57 is set such that the expansion and retraction section 52 or the distal end side of the insertion portion 2 is movable forward and backward within the range of 20 mm or more and 100 mm or less.

Hereinafter, one example of the above-described ESD procedure will be briefly described, with reference to FIGS. 8 and 9.

FIGS. 8A to 8D are perspective views schematically illustrating one example of an incision operation of a lesional mucosa part in the ESD in which the endoscope system in FIG. 1 is inserted into the subject and the procedure is performed by using the incision tool and the high-frequency knife protruded from the channel of the endoscope. FIG. 8A is a perspective view illustrating the procedure for forming a hole on the mucosa around the lesional mucosa part with an incision tool, FIG. 8B is a perspective view illustrating the state where the high-frequency knife is protruded into the subject through the channel of the endoscope, FIG. 8C is a perspective view illustrating the state where the distal end of the high-frequency knife in FIG. 8B is inserted in the hole formed by the incision tool, and FIG. 8D is a perspective view illustrating the incision operation of the lesional mucosa part with the high-frequency knife.

In addition, FIGS. 9A and 9B are perspective views schematically describing the dissection operation of the lesional mucosa site in the ESD with the dissection tool protruded from the channel of the endoscope. FIG. 9A is a perspective view illustrating the state where the distal end of the dissection tool is hooked on the slit formed by the incision with the high-frequency knife, and FIG. 9B is a perspective view illustrating an operation of adjusting a direction of a flexing portion of the dissection tool in FIG. 9A.

First, the surgeon introduces the endoscope system 100 into the subject, and thereafter injects medicinal solution such as normal saline into the submucosal layer of the lesional mucosa part S, which is a tissue to be treated, using an injection needle, not shown, inserted from the treatment instrument insertion port 13, passed through the channel 2*n*, and protruded from the distal end surface 2*sm* of the distal end portion 2*s* into the subject, to thereby cause the lesional mucosa part S to bulge, as shown in FIG. 8A. Note that the diameter of the lesional mucosa part S which is subjected to the ESD procedure is assumed to be about 20 mm to 50 mm, as is well known.

Next, as shown in FIG. 8A, the surgeon forms a hole H on a part of the mucosa around the lesional mucosa part S through the use of the incision tool 112 inserted from the treatment instrument insertion port 13, passed through the channel 2*n*, and protruded from the distal end surface 2*sm* of the distal end portion 2*s* into the subject.

After that, the surgeon extracts the incision tool 112 from the channel 2*n*, as shown in FIG. 8B, and inserts the knife distal end of the high-frequency knife 113 inserted from the treatment instrument insertion port 13, passed through the channel 2*n*, and protruded from the distal end surface 2*sm* of the distal end portion 2*s* into the subject into the hole H, as shown in FIG. 8C.

In this state, the surgeon moves the distal end side of the insertion portion 2 forward and backward by approximately 20 mm to 50 mm with the aid of the bending of the bending portion 2*w*, while applying high-frequency current to the knife distal end, to thereby move also the distal end side of the high-frequency knife 113 forward and backward by approximately 20 mm to 50 mm and incise the periphery of the lesional mucosa part S, and then forms a slit P, as shown in FIG. 8D.

Next, the surgeon incises the lesional mucosa part S over the entire circumference thereof, and thereafter extracts the high-frequency knife 113 from the channel 2*n*. Then, as shown in FIG. 9A, the surgeon introduces, into the subject, the dissection tool 114, which is inserted from the treatment instrument insertion port 13, passed through the channel 2*n*, and protruded from the distal end surface 2*sm* of the distal end portion 2*s* into the subject. After that, the surgeon causes a knife portion 114*n* to abut against the slit P to hook a flexing portion 114*k*, and incises and dissects the lower layer of the lesional mucosa part S. At this time, the flexing portion 114*k* is preferably parallel with the muscularis propria or directed to the inner cavity side.

Note that, if the direction of the flexing portion 114*k* is not preferable, the surgeon adjusts the direction of the flexing portion 114*k*. Specifically, as shown in FIG. 9B, the surgeon grasps a sheath 114*s* to rotate an operation portion 114*a* in the state where an operation slider 114*b* of the operation portion 114*a* is slightly moved rearward. Subsequently, the surgeon changes the direction of the flexing portion 114*k*, and thereafter moves the operation slider 114*b* forward. As a result, the rotational movement of the knife portion 114*n* is restricted by a known mechanism. Accordingly, the flexing portion 114*k* is fixed with the direction thereof being maintained during the resection and dissection of the mucosa.

Finally, the surgeon resects and dissects the entirety of the lesional mucosa part S, and thereafter extracts the dissection tool 114 from the channel 2*n*, to take out the lesional mucosa part S through the channel 2*n*, with a grasping forceps or the like, not shown, inserted from the treatment instrument insertion port 13, passed through the channel 2*n*, and protruded in the subject from the distal end surface 2*sm* of the distal end portion 2*s*.

Note that the configuration of the endoscope system 100 according to the present embodiment is effective, in particular, in the procedure of above-described ESD shown in FIG. 8D.

Specifically, the configuration is effective in particular when the surgeon would like to move the distal end side of the insertion portion 2 by 20 mm to 50 mm as in the procedure of ESD shown in FIG. 8D, in the state where the position of the distal end side of the insertion portion 2 is fixed to the intestinal wall of the large intestine B, for example, by expanding the expanding and contracting portion 52*a* of the expansion and retraction section 52 and the lesional mucosa part S is observed with the optical system of the endoscope 1.

Since the attaching portion 52*b* is loosely fitted to the outer circumference 2*kg* in the present embodiment, in the state where the expanding and contracting portion 52*a* is expanded, if the surgeon releases his or her hand from the insertion portion 2 or reduces a force for pushing the insertion portion 2, the insertion portion 2 will be caused to move greatly toward the anus side due to the peristaltic movement of the large intestine, as described above.

However, in the present embodiment, the attaching portion 52*b* is configured to abut against the ring-shaped member 57. Such a configuration prevents the large retreating movement (exceeding 100 mm) of the insertion portion 2, to thereby prevent the surgeon from losing sight of the lesional mucosa part S.

For these reasons, the predetermined space E1 in the longitudinal direction E between the ring-shaped member 56 and the ring-shaped member 57 is set such that the expansion and retraction section 52 or the distal end side of the insertion portion 2 is movable forward and backward within a range of 20 mm or more and 100 mm or less which is a moving range necessary and sufficient for the size of the lesional mucosa part S to which the ESD can be applied.

The reason why the moving range is set so as not to exceed 100 mm that, if the moving amount of the distal end side of the insertion portion 2 is too large, the retreating amount of the insertion portion 2 due to the peristaltic movement becomes large, as described above, and even if the expanding and contracting portion 52*a* is expanded, the fixing effect of the distal end side of the insertion portion 2 in the subject is reduced.

In addition, as shown in FIGS. 2 and 3, the rotational movement restriction portions 52 at are two protrusions provided on the inner circumferential surface of the ring-shaped attaching portion 52*b* so as to be located in the gap R3 and separated from each other by approximately 180 degrees in the outer circumferential direction C.

In addition, the rotational movement restriction portion 55 is a protrusion directly fixed to the outer circumference 2*kg* of the flexible tube portion 2*k*, not through another member and having a distal end fixed to the ring-shaped member 56 and a proximal end fixed to the ring-shaped member 57, the rotational movement restriction portion 55 having the predetermined space E1 between the distal end and proximal end along the longitudinal direction E and being located in the gap R3.

Note that the rotational movement restriction portion 55 may be provided at only either the ring-shaped members 56, 57 or the outer circumference 2kg, and furthermore the rotational movement restriction portion 55 does not have to connect the ring-shaped members 56 and 57 along the longitudinal direction E.

The rotational movement restriction portions 52at and 55 restrict the angle in which the expansion and retraction section 52 rotationally moves in the outer circumferential direction C on the outer circumference of the insertion portion 2.

Specifically, the rotational movement restriction portions 52at and 55 configured to restrict the angle such that the expansion and retraction section 52 rotationally moves within a defined range of plus or minus 180 degrees or less along the outer circumferential direction C by each of the rotational movement restriction portions 52at abutting against the rotational movement restriction portion 55 in the outer circumferential direction C. That is, the rotational movement restriction portions restrict the angle such that the expansion and retraction section 52 rotates in one direction or the other direction along the outer circumferential direction C within the defined range of 180 degrees or less.

More specifically, in the state where the expanding and contracting portion 52a is expanded in the subject and held by the inner wall of the subject, the rotational movement restriction portions 52at and 55 restrict the rotational movement angle such that the expansion and retraction section 52 or the distal end side of the insertion portion 2 does not rotationally move plus or minus 180 degrees or more by the rotational movement restriction portion 55 abutting, in the outer circumferential direction C, against one of the two rotational movement restriction portions 52at provided separated from each other by approximately 180 degrees in the outer circumferential direction C.

In the configuration of the present embodiment, the attaching portion 52b of the expansion and retraction section 52 is loosely fitted to the outer circumference of the insertion portion 2. As described above, since the surgeon inserts the insertion portion 2 into the large intestine B while twisting the insertion portion 2, for example, if the rotational movement restriction portions 52at and 55 are not provided, when the surgeon releases his or her hand from the insertion portion 2, the insertion portion 2 rotationally moves more than 360 degrees in the outer circumferential direction C with respect to the expansion and retraction section 52 even if the expanding and contracting portion 52a is expanded, and as a result, the surgeon loses sight of the lesional mucosa part S and tubular fluid conduit 53 gets entangled with the outer circumference of the insertion portion 2.

Note that the above-described configurations of the rotational movement restriction portions 52at and 55 are just one example, and not limited to the above-described configurations as long as the rotational movement restriction portions are configured to be capable of restricting the rotational movement angle of the distal end side of the insertion portion 2 with respect to the expansion and retraction section 52 to a defined range of plus or minus 180 degrees or less.

Thus, in the present embodiment, the expansion and retraction section 52 that includes the expanding and contracting portion 52a configured to be expandable and contractible is movable forward and backward in the predetermined space E1 in the longitudinal direction E, which is defined by the ring-shaped members 56 and 57 fixed to the outer circumference of the insertion portion 2. In addition, the expansion and retraction section 52 is provided such that the rotational movement angle thereof in the outer circumferential direction C is restricted by the rotational movement restriction portions 52at and 55.

According to such a configuration, even in the state where the expanding and contracting portion 52a of the expansion and retraction section 52 is expanded and held by the inner wall of the subject, the distal end side of the insertion portion 2 is movable forward and backward within the range of 20 mm to 100 mm defined by the ring-shaped members 56 and 57. In addition, the distal end side of the insertion portion 2 may be configured to be rotationally movable within the range of plus or minus 180 degrees or less, which is defined by the rotational movement restriction portions 52at and 55, to achieve smooth rotational movement.

With such a configuration, in the above-described ESD and the like, treatment for moving the distal end side of the insertion portion 2 by about 20 mm to 50 mm in the longitudinal direction E in the state where the position of the distal end side of the insertion portion 2 is fixed to some extent and the lesional mucosa part S is observed can be performed easily without contracting the expanding and contracting portion 52a as required in the conventional configuration.

In addition, even if the surgeon releases his or her hand from the insertion portion 2 or reduces a force for pushing the insertion portion 2, the attaching portion 52b of the expansion and retraction section 52 abuts against either the ring-shaped member 56 or the ring-shaped member 57. Therefore, in the state where the expanding and contracting portion 52a is expanded, the distal end side of the insertion portion 2 does not greatly move forward and backward, which is capable of preventing the surgeon from losing sight of the lesional mucosa part S.

Furthermore, in the present embodiment, the ring-shaped members 56, 57, the expansion and retraction section 52, and the rotational movement restriction portions 52at, 55 are directly provided to the outer circumference of the insertion portion 2 without using another member such as a conventional overtube.

Therefore, when the endoscope system 100 is inserted into the large intestine B, for example, the parts that contact the anus are only the outer circumference of the insertion portion 2 and the fluid conduit 53, and the parts closely contact the anus. Such a configuration is capable of surely preventing the filth in the large intestine B from leaking outside the subject through the anus, and ensuring the movability and rotatability of the insertion portion 2 in the large intestine B in a preferable manner since an overtube is not used.

Thus, it is possible to provide the insertion portion mounted tool 50 of the endoscope having improved operability and the endoscope system 100 that are configured to be capable of maintaining the position of the distal end side of the insertion portion 2 in the subject so as to be movable in the longitudinal direction E and the outer circumferential direction C within the predetermined range required for treatment and preventing the leakage of the filth from the subject.

Note that modified examples of the first embodiment will be described below.

In the above-described present embodiment, the expansion and retraction section 52 is movable forward and backward within the range defined by the ring-shaped members 56 and 57 by the attaching portion 52b being loosely fitted to the outer circumference of the insertion portion 2. However, the configuration of the expansion and retraction section 52 is not limited to the above-described one, and may be movable forward and backward within the range defined by the ring-shaped members 56 and 57 and rotationally movable in the outer circumferential direction C by the attaching portion 52b abutting against the outer circumference of the insertion portion 2 through a bearing or the like.

Figure 10:
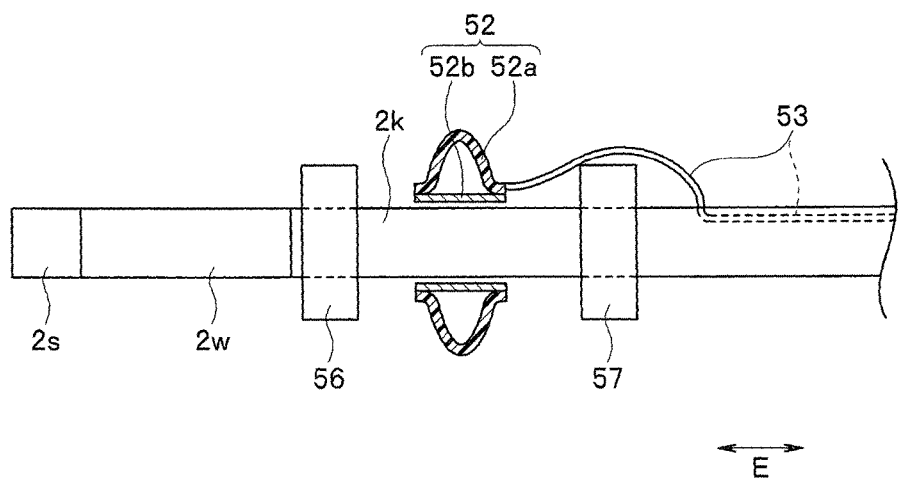
FIG. 10 is a view schematically illustrating a modified example of the endoscope system, in which a part of a fluid conduit in FIG. 2 is provided in the insertion portion.

In addition, another modified example will be described below with reference to FIG. 10. FIG. 10 is a view schematically illustrating a modified example of the endoscope system, in which a part of the fluid conduit in FIG. 2 is provided in the insertion portion.

As shown in FIG. 10, the fluid conduit 53 is provided in the insertion portion 2 and may be exposed outside the insertion portion 2 from near the rear part of the ring-shaped member 57 and the distal end of the fluid conduit 53 may be connected to the expanding and contracting portion 52a. Note that an existing conduit provided in the insertion portion 2 may be used also as the fluid conduit 53.

Such a configuration is capable of surely preventing the fluid conduit 53 from getting entangled with the outer circumference of the insertion portion 2 when the insertion portion 2 or the expansion and retraction section 52 is rotationally moved. Note that other configurations and effects are the same as those in the above-described present embodiment.

Figure 11:
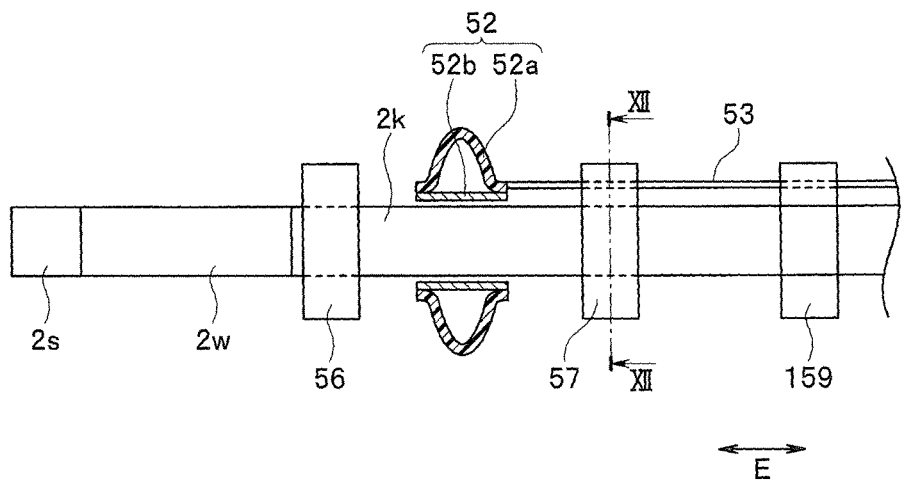
FIG. 11 is a view schematically illustrating a configuration in a modified example of the endoscope system, in which a fluid conduit passes through the ring-shaped member positioned at the rear side in the positioning portion in FIG. 2.

Furthermore, another modified example will be shown below with reference to FIGS. 11 and 12. FIG. 11 is a view schematically illustrating a configuration in a modified example of the endoscope system, in which a fluid conduit passes through the ring-shaped member positioned at the rear side in the positioning portion in FIG. 2, and FIG. 12 is a cross-sectional view of the endoscope system along the line XII-XII in FIG. 11.

Figure 12:
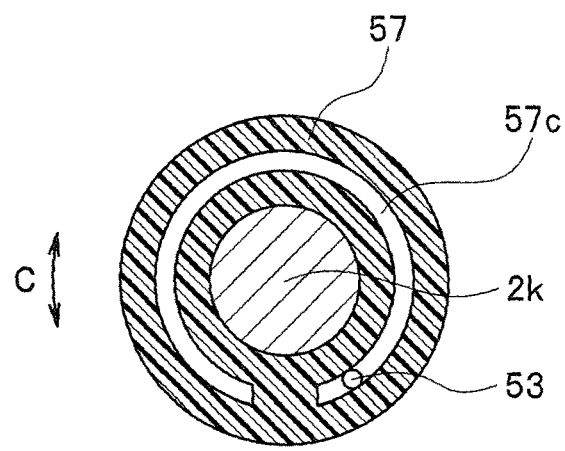
FIG. 12 is a cross-sectional view of the endoscope system along line XII-XII in FIG. 11.

As shown in FIGS. 11, 12, the ring-shaped member 57 may include a space 57c, a cross section of which is substantially C-shape, in which the fluid conduit 53 is movable in the outer circumferential direction C within plus or minus 180 degrees.

According to such a configuration, similarly in the above-described present embodiment, even if the fluid conduit 53 is provided outside the insertion portion 2, the fluid conduit 53 moves in the outer circumferential direction C in the space 57c within the range of plus or minus 180 degrees in accordance with the rotational movement of the insertion portion 2 or the expansion and retraction section 52, which is surely capable of preventing the fluid conduit 53 from getting entangled with the outer circumference of the insertion portion 2. Note that other configurations and effects are the same as those in the above-described present embodiment.

In addition, as shown in FIG. 11, one or a plurality of alignment members 159 having a configuration same as that of the ring-shaped member 57 may be provided on the outer circumference of the insertion portion 2 at a position on the more rear side than the ring-shaped member 57. Such a configuration is capable of more effectively preventing the fluid conduit 53 from getting entangled with the outer circumference of the insertion portion 2.

Figure 13:
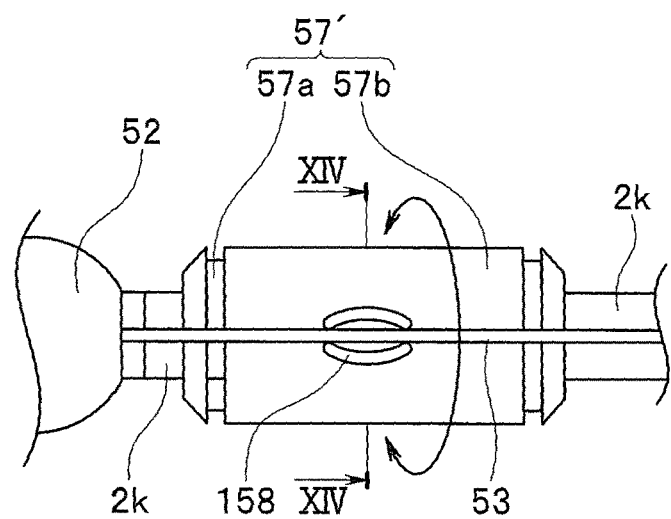
FIG. 13 is a view schematically illustrating a modified example of the endoscope system, in which the ring-shaped member positioned at the rear side in the positioning portion in FIG. 2 is made of a double pipe.

In addition, another modified example will be shown below with reference to FIGS. 13, 14. FIG. 13 is a view schematically illustrating a modified example of the endoscope system, in which the ring-shaped member positioned at the rear side in the positioning portion in FIG. 2 is made of a double pipe, and FIG. 14 is a cross-sectional view of the endoscope system along the line XIV-XIV in FIG. 13.

Figure 14:
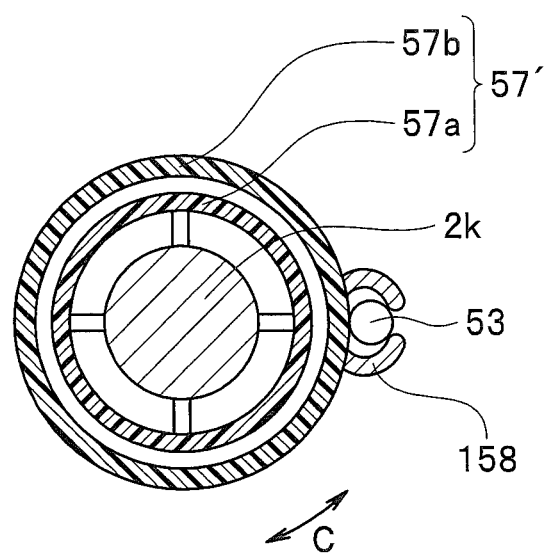
FIG. 14 is a cross-sectional view of the endoscope system along line XIV-XIV in FIG. 13.

As shown in FIGS. 13, 14, a ring-shaped member 57' located behind the expansion and retraction section 52 includes an inner pipe 57a fixed to the outer circumference of the insertion portion 2 and an outer pipe 57b provided in a loosely-fitted manner so as to be rotationally movable with respect to the outer circumference of the inner pipe 57a, and a retaining holder 158 of the fluid conduit 53 may be provided on the outer circumferential surface of the outer pipe 57b.

Note that the outer pipe 57b is prevented from coming off from the outer circumference of the inner pipe 57a in the longitudinal direction E by stoppers provided respectively at the distal end and the proximal end of the outer circumferential surface of the inner pipe 57a.

Also according to such a configuration, similarly as the configurations shown in FIGS. 11 and 12, even if the fluid conduit 53 is provided outside the insertion portion 2, the fluid conduit 53 is surely prevented from getting entangled with the outer circumference of the insertion portion 2 when the insertion portion 2 or the expansion and retraction section 52 is rotationally moved. Note that other configurations and effects are the same as those in the above-described present embodiment.

Figure 15:
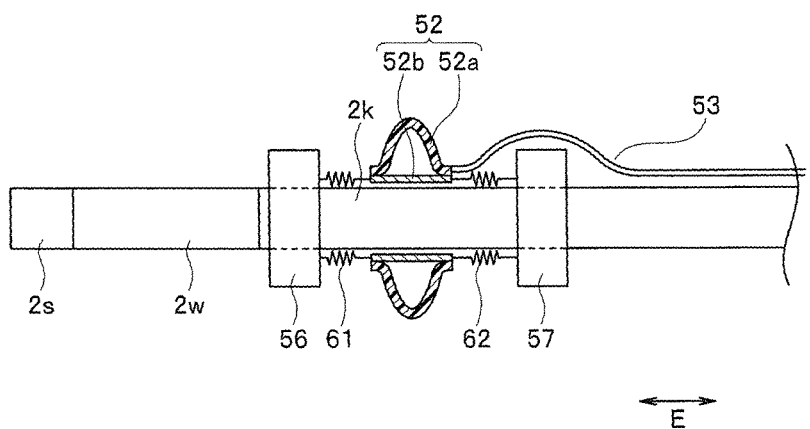
FIG. 15 is a view schematically illustrating a modified example of the endoscope system, in which a position returning member is provided between each of the ring-shaped members and the expansion and retraction section in an extending direction on the outer circumference of the insertion portion in FIG. 2.

Furthermore, another modified example will be shown below with reference to FIG. 15. FIG. 15 is a view schematically illustrating a modified example of the endoscope system, in which a position returning member is provided between each of the ring-shaped members and the expansion and retraction section in an extending direction on the outer circumference of the insertion portion in FIG. 2.

As shown in FIG. 15, a position returning member 61 such as a coil spring having a distal end fixed to the ring-shaped member 56 and a proximal end fixed to the expansion and retraction section 52 may be provided to the outer circumference of the insertion portion 2 so as to be located between the ring-shaped member 56 and the expansion and retraction section 52 in the longitudinal direction E, and a position returning member 62 such as a coil spring having a proximal end fixed to the ring-shaped member 57 and a distal end fixed to the expansion and retraction section 52 may be provided to the outer circumference of the insertion portion 2 so as to be located between the ring-shaped member 57 and the expansion and retraction section 52 in the longitudinal direction E.

Note that the position returning members 61, 62 are not limited to the coil springs but may be damper structures in which fluid is sealed or urging members made of resin having elasticity.

With such a configuration, when the surgeon releases his or her hand from the insertion portion 2, in the case where the expanding and contracting portion 52a of the expansion and retraction section 52 is expanded and held by the inner wall, the position of the insertion portion 2 returns to a reference position shown in FIG. 15 with the position returning members 61, 62, and in the case where the expanding and contracting portion 52a is contracted, the position of the expansion and retraction section 52 returns to the reference position shown in FIG. 15 with the position returning members 61, 62.

Such a configuration improves not only the observation performance and treatment performance but also operability, since it is possible to resist a force that moves the insertion portion 2 toward the anus, which is generated by the above-described peristaltic movement, when the expanding and contracting portion 52a is expanded. Note that other configurations and effects are the same as those in the above-described present embodiment.

Figure 16:
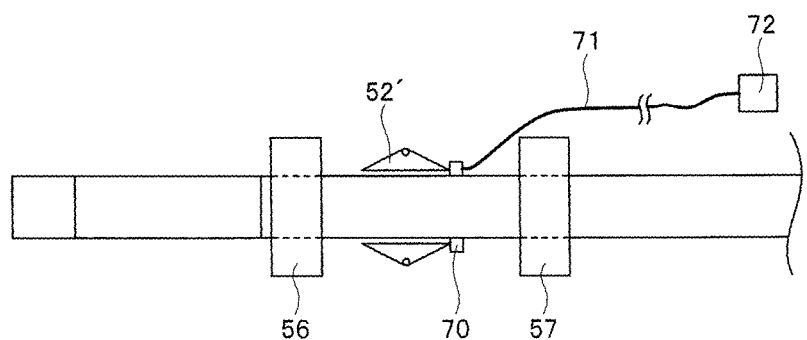
FIG. 16 is a view schematically illustrating a modified example of the insertion system, in which the expansion and retraction section in FIG. 2 is made of a spring member.
Figure 17:
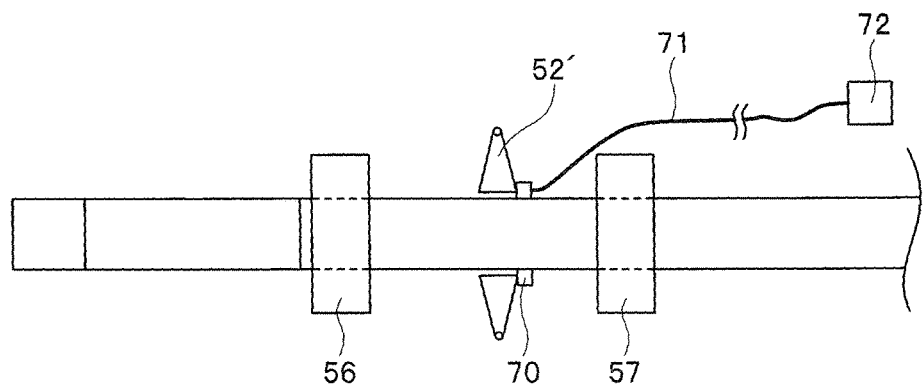
FIG. 17 is a view schematically illustrating a state where the spring member in FIG. 16 is extended.

Note that another modified example will be shown below with reference to FIGS. 16 and 17. FIG. 16 is a view schematically illustrating a modified example of the insertion system, in which the expansion and retraction section in FIG. 2 is made of a spring member, and FIG. 17 is a view schematically illustrating a state where the spring member in FIG. 16 is extended.

In the above-described present embodiment, the expansion and retraction section 52 is described by taking the case where the expansion and retraction section 52 is made of a balloon configured to be expandable and contractible in accordance with the supply and discharge of the fluid through the fluid conduit 53, as an example.

The expansion and retraction section is not limited to the example. As shown in FIGS. 16 and 17, an expansion and retraction section 52' may be configured by a bar-shaped or a plate-shaped spring member mechanically expandable and contractible like a pantograph, in accordance with application and shutdown of the power from a controller 72 through a signal line 71.

Note that, in such a configuration, the signal line 71 is applicable to the modified examples shown in FIGS. 10 to 14, similarly as the fluid conduit 53.

In addition, the signal line 71 may include a function for sending a signal to a valve for switching application and shutdown of the fluid to the expanding and contracting portion 52a by being combined with the fluid conduit 53 in the present embodiment.

Furthermore, the configuration of the expansion and retraction section 52' is not limited to the above-described configuration, and the expansion and retraction section 52' may be applicable to any configuration as long as the expansion and retraction section is expandable and contractible.

Also such a configuration enables the same effects as those in the present embodiment to be obtained. Note that other configurations and effects are the same as those in the present embodiment.

Second Embodiment

Figure 18:
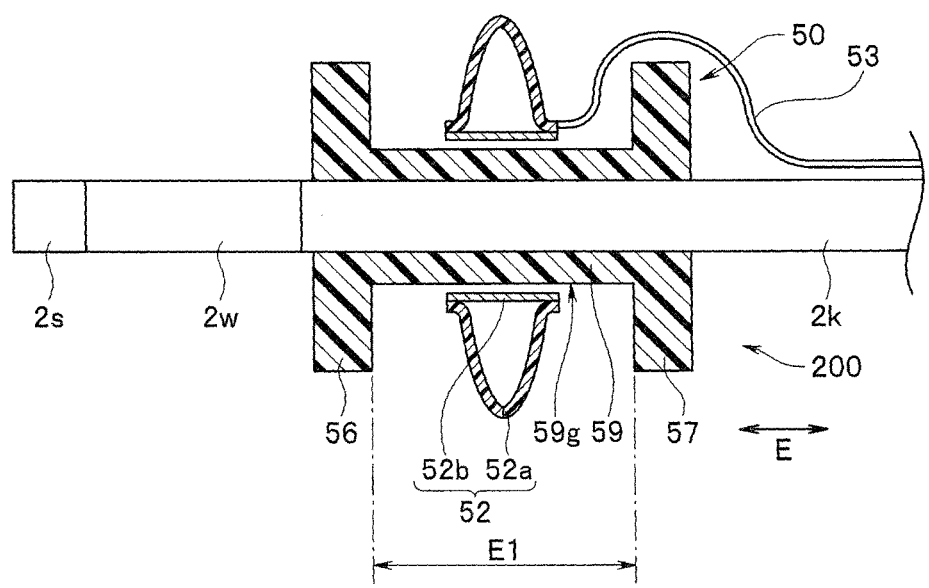
FIG. 18 is a partial cross-sectional view schematically illustrating a part of an endoscope system including an insertion portion mounted tool of an endoscope according to a second embodiment.

FIG. 18 is a partial cross-sectional view schematically illustrating a part of an endoscope system including an insertion portion mounted tool of an endoscope according to the present embodiment.

The configurations of the endoscope system and the insertion portion auxiliary mounted tool of endoscope according to the second embodiment are different from those of the endoscope system and the insertion portion mounted tool of endoscope according to the first embodiment as shown in FIGS. 1 to 17 in that a positioning portion, an expansion and retraction section, and rotational movement restriction portions are configured as an integrated mounting unit. Therefore, the same components as those in the first embodiment are attached with the same reference signs and description thereof will be omitted.

As shown in FIG. 18, in the present embodiment, the ring-shaped members 56, 57, the expansion and retraction section 52, and rotational movement restriction portions, not shown, are configured as an integrated mounting unit 200 that is assembled in advance, and the mounting unit 200 is fixed to the position, which is shown in the first embodiment, on the outer circumference of the insertion portion 2.

Specifically, the ring-shaped member 56 and the ring-shaped member 57 are coupled with each other in the longitudinal direction E with a tubular coupling member 59 directly fixed to the outer circumference of the insertion portion 2, and the expansion and retraction section 52 is loosely fitted to an outer circumference 59g of the coupling member 59 and configured to be movable forward and backward within the range having the predetermined space E1 restricted by the ring-shaped members 56, 57 on the outer circumference 59g and rotationally movable in the outer circumferential direction C.

Note that, though not shown, the rotational movement angle of the insertion portion 2 or the expansion and retraction section 52 is restricted also in the present embodiment, similarly as in the first embodiment, by the rotational movement restriction portions 52at provided to the expansion and retraction section 52 and the rotational movement restriction portion provided on the outer circumference 59g abut against each other in the outer circumferential direction C. Note that other configurations are the same as those in the first embodiment.

With such a configuration, the ring-shaped members 56, 57, the expansion and retraction section 52, and the rotational movement restriction portions are configured as a single integrated mounting unit 200. Therefore, such a configuration enables the number of the components mounted to the outer circumference of the insertion portion 2 to be reduced to one member from three members in the first embodiment, to thereby improve the mounting performance of the insertion portion mounted tool 50 to the outer circumference of the insertion portion 2. Note that other effects are the same as those in the first embodiment.

In addition, in the first and second embodiments, the insertion instrument is described by taking the medical endoscope 1 as an example, but is not limited to the same. The embodiments are applicable not only to an industrial endoscope 1 but also to the insertion instrument such as treatment instrument other than the endoscope 1.

Therefore, the insertion portion mounted tool 50 can be mounted to an insertion portion of an insertion instrument such as a treatment instrument other than an endoscope, and applicable to an insertion system using an insertion instrument such as a treatment instrument other than an endoscope.

What is claimed is:

1. An insertion portion mounted tool of an insertion instrument, the insertion portion mounted tool being configured to be mounted to an insertion portion of the insertion instrument, the insertion portion being configured to be inserted into a subject, the insertion portion mounted tool comprising:

an expansion and retraction section provided on an outer circumferential side of the insertion portion so as to be movable forward and backward in a longitudinal direction of the insertion portion, the expansion and contraction section being configured to be expanded in the subject by an operation from outside of the subject to thereby be held by an inner wall of the subject;

a positioning portion that defines a range in which the expansion and retraction section is movable forward and backward in the longitudinal direction with respect to the insertion portion; and a rotational movement restriction portion that restricts an angle greater than zero in which the expansion and retraction section is rotationally moved in an outer circumferential direction of the insertion portion on an outer circumference of the insertion portion.

2. The insertion portion mounted tool of the insertion instrument according to claim 1, wherein the expansion and retraction section is provided so as to be rotationally movable with respect to the outer circumference of the insertion portion by an angle within a range restricted by the rotational movement restriction portion.

3. The insertion portion mounted tool of the insertion instrument according to claim 1, wherein the rotational movement restriction portion is configured to restrict the angle such that the expansion and retraction section is rotationally moved in a defined range of more than zero degrees and less than 180 degrees along the outer circumferential direction.

4. The insertion portion mounted tool of the insertion instrument according to claim 3, wherein the rotational movement restriction portion comprises:
a first abutting portion provided to the positioning portion;
wherein the first abutting portion is configured to abut against a second abutting portion provided on the outer circumference of the insertion portion in the outer circumferential direction.

5. The insertion portion mounted tool of the insertion instrument according to claim 1, wherein
the positioning portion, the expansion and retraction section, and the rotational movement restriction portion are configured as an integrated mounting unit, and
the mounting unit is fixed to the outer circumference of the insertion portion.

6. The insertion portion mounted tool of an insertion instrument according to claim 5,
wherein the positioning portion comprises two ring-shaped members fixed to the outer circumference of the insertion portion with a predetermined space between each other in the longitudinal direction, and the two ring-shaped members are coupled to each other with a coupling member, and
the expansion and retraction section is configured to be movable forward and backward in the longitudinal direction in a range of the predetermined space on the outer circumference of the coupling member, the range being restricted by the two ring-shaped members.

7. The insertion portion mounted tool of the insertion instrument according to claim 1, wherein the positioning portion is configured to be fixed to a position of the outer circumference of the insertion portion such that the range in which the expansion and retraction section moves in the longitudinal direction with respect to the outer circumference of the insertion portion is restricted to a part other than a bending portion provided on a distal end side in the longitudinal direction of the insertion portion.

8. The insertion portion mounted tool of the insertion instrument according to claim 7, wherein
the positioning portion comprises two ring-shaped members configured to be fixed to the outer circumference of the insertion portion with a predetermined space between each other in the longitudinal direction, and
the ring-shaped member positioned at a front side in the longitudinal direction is configured to be fixed to immediately behind a proximal end of the bending portion in the longitudinal direction.

9. The insertion portion mounted tool of the insertion instrument according to claim 1, wherein the positioning portion, the expansion and retraction section, and the rotational movement restriction portion are configured to be directly provided to the outer circumference of the insertion portion in a predetermined region on a distal end side in the longitudinal direction of the insertion portion.

10. The insertion portion mounted tool of the insertion instrument according to claim 1, wherein the positioning portion sets the range in which the expansion and retraction section moves in the longitudinal direction to a range of 20 mm to 100 mm.

11. An insertion system comprising:
the insertion portion mounted tool of the insertion instrument according to claim 1; and
the insertion instrument including the insertion portion to which the insertion portion mounted tool of the insertion instrument is mounted.

* * * * *